US011322008B2

(12) United States Patent
Burton et al.

(10) Patent No.: US 11,322,008 B2
(45) Date of Patent: *May 3, 2022

(54) IMPACT DETECTION

(71) Applicant: Rheon Labs Ltd, London (GB)

(72) Inventors: Thomas M W Burton, London (GB); Daniel James Plant, London (GB)

(73) Assignee: RHEON LABS LTD., London (GB)

(*) Notice: Subject to any disclaimer, the term of this patent is extended or adjusted under 35 U.S.C. 154(b) by 0 days.

This patent is subject to a terminal disclaimer.

(21) Appl. No.: 17/064,440

(22) Filed: Oct. 6, 2020

(65) Prior Publication Data

US 2021/0020015 A1    Jan. 21, 2021

Related U.S. Application Data

(63) Continuation of application No. 16/405,776, filed on May 7, 2019, now Pat. No. 10,810,852.

(30) Foreign Application Priority Data

May 9, 2018 (GB) ..................... 1807571

(51) Int. Cl.
*G08B 21/02* (2006.01)
*G08B 21/24* (2006.01)

(52) U.S. Cl.
CPC ............ *G08B 21/02* (2013.01); *G08B 21/24* (2013.01)

(58) Field of Classification Search
None
See application file for complete search history.

(56) References Cited

U.S. PATENT DOCUMENTS

| | | | |
|---|---|---|---|
| 10,413,009 B2* | 9/2019 | McGuckin, Jr. | ...... G01L 5/0052 |
| 2012/0210498 A1 | 8/2012 | Mack | |
| 2013/0072765 A1 | 3/2013 | Kahn et al. | |
| 2013/0149969 A1 | 6/2013 | Smailagic et al. | |
| 2014/0018686 A1 | 1/2014 | Medelius et al. | |
| 2017/0031334 A1* | 2/2017 | Medelius | ............... A61B 5/369 |
| 2017/0055881 A1 | 3/2017 | Kang et al. | |
| 2017/0172222 A1 | 6/2017 | Morgenthau et al. | |
| 2017/0325683 A1 | 11/2017 | Larson et al. | |
| 2018/0227959 A1 | 8/2018 | Fraccaroll | |

FOREIGN PATENT DOCUMENTS

| | | |
|---|---|---|
| EP | 3246888 A1 | 11/2017 |
| GB | 2528996 A | 2/2016 |
| WO | 2016134306 A1 | 8/2016 |

OTHER PUBLICATIONS

Search Report for United Kingdom Patent Application No. GB1807571.3; dated Nov. 23, 2018, 5 pages.
Search Report for European Patent Application No. 19172894.8, dated Sep. 13, 2019, 9 pages.

* cited by examiner

*Primary Examiner* — Adolf Dsouza
(74) *Attorney, Agent, or Firm* — Patterson + Sheridan, LLP

(57) ABSTRACT

An apparatus and methods for impact detection are disclosed. Example apparatus comprises a plurality of sensors. The apparatus is configured to determine whether a user is wearing an item in which the apparatus is comprised, and in response to a positive determination, operate the apparatus in an active operating mode. The active operating mode comprises operating one or more sensors in the plurality to generate data associated with motion of the user at a first sampling rate.

21 Claims, 9 Drawing Sheets

IMPACT DETECTION

CROSS-REFERENCE TO RELATED APPLICATIONS

This Application is a continuation of pending U.S. patent application Ser. No. 16/405,776, filed on May 7, 2019, which claims priority to United Kingdom (GB) Patent Application No. 1807571.3, filed May 9, 2018, the contents of each which are incorporated by reference herein in their entirety.

INTRODUCTION

The present disclosure relates to impact detection. In particular, but not exclusively, the present disclosure relates to apparatus, methods and computer program products for use in impact detection.

Known impact detection systems employ a device with a battery life of approximately 20 hours which uses a gyroscope to monitor if a user of the device has an accident, for example whilst riding a bicycle or a motorcycle. Such known systems have a permanent connection to a mobile telephone and once the power of the device battery is used up, the battery must either be replaced by the user or recharged by the user. Such known systems require user activation for each user activity.

BRIEF SUMMARY

According to a first aspect of the present disclosure, there is provided apparatus comprising a plurality of sensors, the apparatus being configured to: determine whether a user is wearing an item in which the apparatus is comprised; and in response to a positive determination, operate the apparatus in an active operating mode, wherein the active operating mode comprises operating one or more sensors in the plurality to generate data associated with motion of the user at a first sampling rate.

According to a second aspect of the present disclosure, there is provided circuitry comprising a plurality of sensors, the circuitry being configured to: determine whether a user is wearing an item in which the circuitry is comprised; and in response to a positive determination, operate the circuitry in an active operating mode, wherein the active operating mode comprises operating one or more sensors in the plurality to generate data associated with motion of the user at a first sampling rate.

According to a third aspect of the present disclosure, there is provided a method of operating apparatus comprising a plurality of sensors, the method comprising: determining whether a user is wearing an item in which the apparatus is comprised; and in response to a positive determination, operating the apparatus in an active operating mode, wherein the active operating mode comprises operating one or more sensors in the plurality to generate data associated with motion of the user at a first sampling rate.

According to a fourth aspect of the present disclosure, there is provided a computer program comprising a set of instructions, which, when executed by a computerized device comprising a plurality of sensors, cause the computerized device to perform a method comprising: determining whether a user is wearing an item in which the device is comprised; and in response to a positive determination, operating the device in an active operating mode, wherein the active operating mode comprises operating one or more sensors in the plurality to generate data associated with motion of the user at a first sampling rate.

According to a fifth aspect of the present disclosure, there is provided a device comprising a plurality of sensors, the device being configured to: operate the device in one of an active operating mode, a sleep operating mode and a deep sleep operating mode, wherein operating the device in the active operating mode comprises controlling one or more sensors in the plurality to generate data associated with motion of the user at a first sampling rate, wherein operating the device in the sleep operating mode comprises controlling one or more sensors in the plurality to generate data associated with motion of the user at a second sampling rate, the second sampling rate being less than the first sampling rate, and wherein operating the device in the deep sleep operating mode comprises controlling one or more sensors in the plurality to generate data associated with motion of the user at a third sampling rate, the third sampling rate being less than the second sampling rate.

According to a sixth aspect of the present disclosure, there is provided a device comprising an impedance sensor, the device being incorporated into a wearable item, the device being configured to: operate the impedance sensor to measure an impedance associated with the item; and detect whether a user is currently wearing the item on the basis of the measured impedance.

Features described in relation to one aspect of the present disclosure may be incorporated into other aspects of the present disclosure. For example, method embodiments may incorporate any of the features described with reference to apparatus embodiments and vice versa.

BRIEF DESCRIPTION OF THE DRAWINGS

Embodiments of the present disclosure will now be described by way of example only with reference to the accompanying drawings of which.

DETAILED DESCRIPTION

Figure 1:
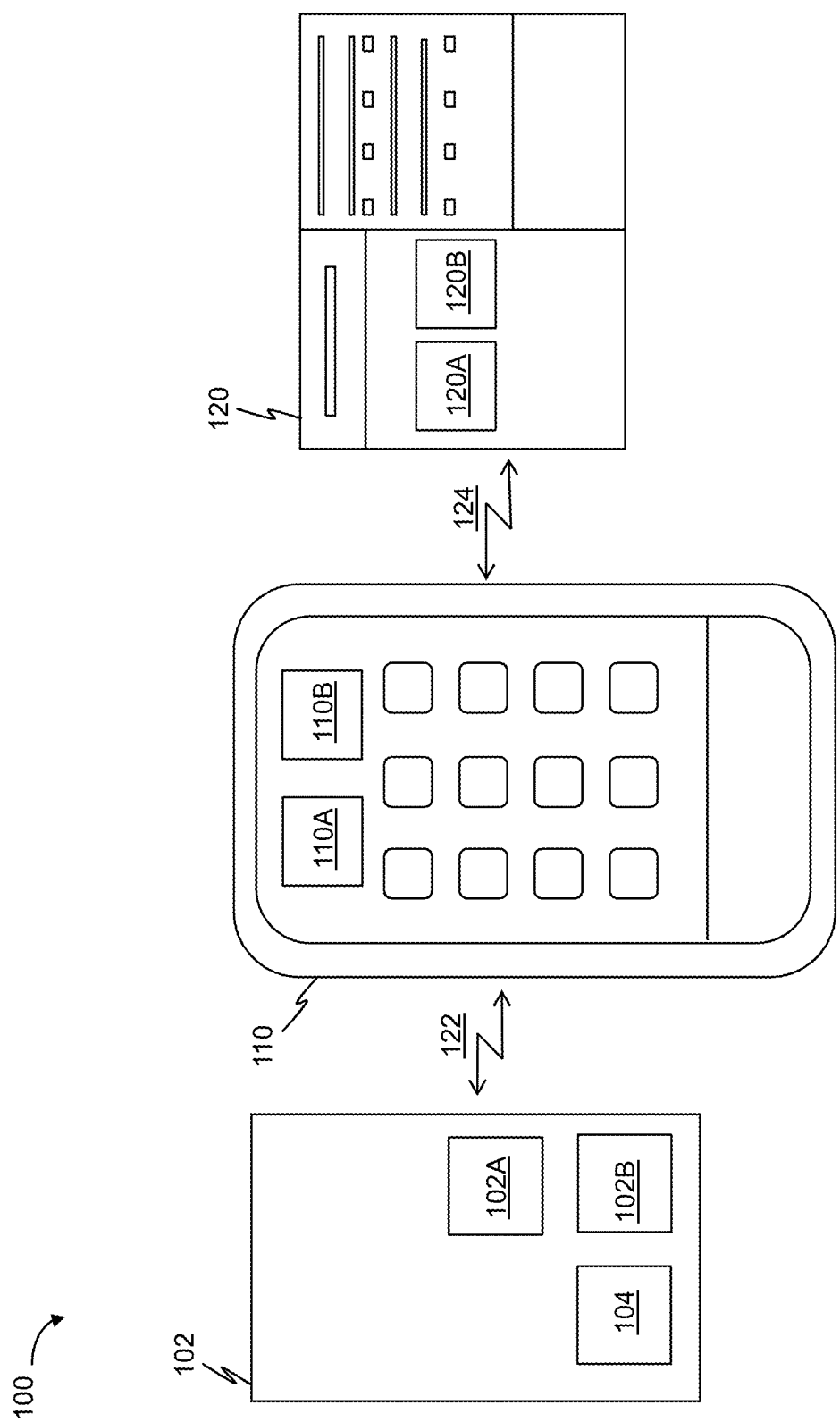
FIG. 1 shows a system diagram according to embodiments.

Embodiments relate to measures, including apparatus, devices, methods and computer programs, for use in impact detection. An impact may for example comprise an impact associated with a user, for example due to the user falling over. An impact may for example comprise a user colliding with another person or object, for example when one or both of the user and the other are using a bicycle, motorbike, car or any other vehicle or craft.

Embodiments provide low power impact detection for use in applications where it is important to be able to detect impacts associated with a user using apparatus (or "a device") comprising a plurality of sensors.

In some applications there may be limited power available which makes it impractical to continuously collect and/or transmit high-resolution data. Embodiments allow identification of when best to connect to a remote device to relay data associated with a detected impact.

Embodiments described herein are suitable for applications where a battery is sealed in with a detection device, for example such that the battery is non-rechargeable and/or non-replaceable.

Pressure fitting battery connections are not suitable for systems which experience high shock loads as this can result in power being cut to the system or forcing a system reset during the period of interest. Embodiments avoid having to change batteries in the apparatus, thus avoiding reliance on pressure fitting battery connections for facilitating such battery changes.

Some embodiments employ apparatus in the form of a Bluetooth Low Energy (BLE) System on Chip (SoC) microcontroller with at least one of an ultra-low power three axis accelerometer, a low power six axis accelerometer and gyroscope, a low power magnetometer, a low power temperature sensor, an impedance sensor (e.g. inductive and/or capacitive) and ancillary circuitry. In some embodiments, the apparatus is fitted with a coin cell battery and sealed in a protective package/enclosure. The protective package helps to damp inbound signals and reduce/remove noise, as well as allowing the apparatus to be worn close to the body of a user.

The protective package can also improve the performance of the device in high shock situations by reducing the peak load transmitted to the device.

The damping characteristics of the protective package can also be tuned to add to the clarity of signal, acting as a form of mechanical low pass filter. If the protective package is heavily damped, the magnitude of the signals transmitted to the device would be reduced which will in turn extend the dynamic range of the device. An optimized protective package with specific damping properties enables the use of simpler commodity sensors as these tend to have lower peak limits for the accelerometer or gyroscope. In cases of heavy impact for example, without a protective package, a sensor could be overloaded, the signal may be clipped and the device may even be damaged. By mechanically damping the input signal(s), the magnitude of the signals could be reduced, enabling the lower magnitude (commodity) sensor to detect the signals without them being clipped, or with a shorter clipping period. If the damping characteristics of the enclosure are known, then signals can be scaled back up to their real value during post-processing. The device has then been used to measure a signal and scale, which the sensor alone normally would not be able to measure. Additionally, the protective package prevents mechanical damage to the device far beyond the protection of equivalent potted boards. Testing has shown that a package allows for more rugged use as well as filtering the signals and dampening noise from the sensors. This also reduces the time that the signal clips and protects the circuit and sensors. This in turn provides better quality data and extends the dynamic range of low power, commoditized sensor chips.

A protective package, made from a damping material, allows the device to survive and measure high G impacts (a high level of deceleration), enabling suitable placement in the head of sports equipment, or in ballistic or blast applications. The damping material may for example comprise a strain rate sensitive material. The materials can completely over-mold the electronics to encapsulate them completely, with little or no change in the data communication range.

If the accelerometer is located on the board at 45 degrees to the primary impact point (often sagittal plane), this further increases the range of the sensors for impacts in the sagittal plane. This enables the sensors to read ($\sqrt{2}$=approx. 1.41) higher sensitivity in the sagittal plane.

Embodiments are able to employ high specification sensors such as a 200 g accelerometer to provide sensing of severe impact incidents. Such a sensor would quickly drain down a device battery if always on, but such power drain becomes manageable due to the power savings from the operating mode switching functionality of embodiments described herein.

In some embodiments, the apparatus is sealed for life such that once activated the device does not need to be charged or have the batteries replaced. Sealing the apparatus ensures the device can be used in damp and dusty environments such as inside body-close protective equipment for sports for example.

In some scenarios, a battery is sealed in with the electronics so that it is non-rechargeable and non-replaceable so it is not practical to continuously collect high-resolution data. To have always-on monitoring of a device transmitting continuously over a wireless link can use a large amount of power which would then require user intervention to remember to change or charge the batteries. Embodiments solve this problem by using one or more (such as an array of) sensors to identify when the apparatus is being actively used and when it is not. This data can then be used to switch between a high power "active" state, a low power "sleep" state and a very low power "deep-sleep" state.

Embodiments allow the use of very low power electronics which in turn means the electronics and the battery can be sealed in a package which does not need charging and which is constantly active. Sealing the device according to embodiments also means that they can be integrated closer to the user's body than previous designs, thus increasing the quality of gathered data.

As the sensor monitors an array of inputs (for example capacitance, movement, temperature), it can also be used as a device to monitor compliance, use or performance parameters. For instance, a sensor can report for example, whether the device is being used at the time of impact or fall or for how long the device is used. This has a number of specific applications, for example employers may wish to know whether employees are wearing their personal protective equipment (PPE), medical professionals may want to know whether patients are wearing medical devices they have been prescribed (for example, a hip protector). Temperature is a good indicator of use that is low power and can be stored from time to time, for example on a BLE chip. When mounted in a helmet, especially near the rear crown, temperature logging can be used to help develop and check the cooling performance of the helmet in hot conditions.

Sealing the apparatus according to embodiments also means that any items (such as clothing) incorporating the apparatus can be washed without damaging the devices. Embodiments can employ a process to detect when the apparatus is being washed (for example by sensing for a sustained high g spin and/or temperature indicative of washing machine water) and manage power use and operation mode accordingly. These sensors have been used in medical trials and experienced no loss of functionality following 30 industrial wash cycles. Wash cycles can be recorded due to sensing a long G>1.0 g (spin cycle) and increased temperature.

Embodiments provide users with "always on" care so that a user need not remember to turn on or otherwise activate the apparatus to an appropriate readiness themselves. This is particularly beneficial for medical applications where elderly or vulnerable users may not remember to or be capable of turning on or re-charging such a device. In addition, this data could be used to understand user wear patterns, alert carers to real-time non-use or collect information about wear compliance.

In embodiments, an array of sensors is used to identify when an item is being worn by a user and monitoring apparatus can be switched to operate in an active monitoring mode to rapidly identify and respond to collision events. Embodiments integrate multiple sensors and process low temporal resolution data gathered during a low power state to predict when the system is being worn by a user.

By overcoming the problem of sealing the system for life, embodiments allow integration of sensors directly into protective equipment such as body armour and helmets which increases the fidelity of the gathered data. This in turn means that embodiments are better able to communicate information about the state of the system and potentially the user as data can be of a higher quality because of the location and proximity to the head or skin of the user.

In addition, by conserving power in this way, embodiments are able to activate to much higher sampling rates during active wear for faster collision detection and greater resolution of the resulting motion of the system including but not limited to acceleration, rotation, temperature, shear and force on a magnetometer.

Embodiments can be employed to monitor for a collision incident which may result in injury to the user, a helmet impact for example, with embedded electronic sensors and transmitters. Embodiments can also be used to track product integrity during its lifetime and can monitor for drops, falls or other incidents which may reduce the effectiveness of a helmet or other protective element. Embodiments allow identification of when a safety device such as a helmet needs replacing.

Embodiments overcome difficulties in long term monitoring for collision incidents where it is important to ensure a body-worn, or body-close, device is monitoring for an impact or collision incident at the correct time without user intervention.

Being able to identify when a wearable item is being worn or used according to embodiments facilitates use of fully sealed-for-life electronics with product lifecycles longer than the expected product they are used within, such as a bicycle helmet for example. By allowing high resolution data to be recorded during a collision incident, embodiments benefit not just the user, but also third parties who have access to this data, such as emergency services and doctors, who can provide appropriate emergency assistance to the user.

FIG. 1 shows a diagram of a system 100 according to embodiments. System 100 comprises apparatus 102, remote device 110 and server 120.

Apparatus 102 comprises a wireless transceiver 102A which is capable of communicating via one or more wireless communication protocols according to embodiments. Apparatus 102 also comprises one or more processors and/or one or more memories 102B which are capable of providing various data processing and data storage/retrieval tasks according to embodiments. Apparatus 102 also comprises a plurality of sensors 104 which are capable of sensing one or more parameters associated with a user (not shown) of apparatus 102. Apparatus 102 may be incorporated into an item (not shown) which is wearable by a user.

Sensors in plurality 104 may for example comprise one or more of a 3-axis or 6-axis inertial sensor such as an accelerometer or gyroscope, a 3-axis magnetometer, an impedance sensor (for example an inductive or capacitive sensor), a thermal sensor for measuring temperature, a shear sensor, a force sensor, a high (such as up to or more than 200 G) accelerometer and a low (such as less than 16 G) accelerometer.

Each of the sensors can operate together or independently.

Apparatus 102 is able to communicate with other devices such as remote device 110 over one or more wireless communication links (or paths) 122. Apparatus 102 may also be able to communicate with other remote devices (not shown) via one or more wired communication links (not shown).

In some embodiments, wireless link 122 comprises a wireless link over which a wireless communication protocol such as BLUETOOTH™, WIFI™, radio frequency identification (RFID), ANT™, ANT+™, ZIGBEE™, infrared (IR), radio, audio, or optical communication technology is employed.

In some embodiments, wireless link 122 comprises a short range wireless link. The term "short" here is used to indicate a relatively short range wireless link compared to a relatively wide (or "long") range wireless link over which a wide range wireless communication protocol (such as a cellular communication protocol) is employed.

In some embodiments, wireless link 124 comprises a wide range wireless link over which various cellular communication protocols (such as Long Term Evolution (LTE)) are employed.

In embodiments, apparatus 102 is encapsulated within a sealed enclosure. In embodiments, the sealed enclosure comprises a strain rate sensitive material. In embodiments, the sealed enclosure comprises an energy absorbing material. In embodiments, apparatus 102 comprises a non-rechargeable battery and the non-rechargeable battery is encapsulated within the sealed enclosure.

Embodiments where apparatus 102 is comprised within an energy absorbing material enclosure provide a "soft" low profile sensor that can be mounted close to the head of a user, thus giving an improved kinematic description of what happens to the head, when compared to an external sensor. Such embodiments are better able to sense/measure rotational impacts.

Remote device 110 comprises a wireless transceiver 110A which is capable of communicating via one or more wireless communication protocols according to embodiments. Remote device 110 also comprises one or more processors and/or one or more memories 110B capable of providing various data processing and data storage/retrieval tasks according to embodiments. Remote device 110 is able to communicate with other devices such as apparatus 102 over wireless communication link 122 and server 120 over wireless communication link 124. Remote device 110 may also be able to communicate with other devices (not shown) via one or more other wireless communicate links (not shown) or one or more wired communication links (not shown).

In embodiments, one or more of wireless links 122 or 124 comprises a radio frequency (RF) wireless link.

In some embodiments, remote device 110 comprises a mobile (cellular) telephone capable of communicating via a mobile telephone network (not shown). In other embodiments, remote device 110 comprises a wireless access point capable of communicating via a packet-switched network (not shown) such as the Internet.

Server 120 comprises one or more wireless and/or wired transceivers 120A which are capable of communicating via one or more wireless or wired communication protocols according to embodiments. Server 120 may be connected to one or more packet switched communication networks (not shown) which operate an Internet Protocol (IP). Server 120 also comprises one or more processors and/or one or more memories 120B capable of providing various data processing and data storage/retrieval tasks according to embodiments.

In embodiments, apparatus 102 is configured to determine whether a user is wearing an item in which the apparatus is comprised. In response to a positive determination (i.e. the user is determined to be wearing the item), apparatus 102 is configured to operate in an active operating mode. The active operating mode comprises operating one or more sensors in the plurality of sensors 104 to generate data associated with motion of the user at a first sampling rate.

In embodiments, apparatus 102 is configured to operate at least one sensor in the plurality 104 to perform the determination. In some such embodiments, the at least one sensor comprises an impedance sensor operable to determine whether the user is wearing the item by sensing an impedance indicative of the user wearing the item. In embodiments, a sensed impedance above a predetermined threshold is indicative of the user wearing the item. In embodiments, a sensed impedance below a predetermined threshold is indicative of the user not wearing the item.

In embodiments, the at least one sensor comprises at least one accelerometer operable to determine whether the user is wearing the item by sensing movement and orientation of apparatus 102 indicative of the user wearing the item. In embodiments, movement of apparatus 102 and apparatus 102 being orientated in a predefined way up are indicative of the user wearing the item. In embodiments, movement of apparatus 102 and apparatus 102 being orientated differently from the predefined way up are indicative of the user not wearing the item. In embodiments, no sensed movement of apparatus 102 is indicative of the user not wearing the item.

In embodiments, the at least one sensor comprises at least one temperature sensor operable to determine whether the user is wearing the item by sensing a temperature of one or more of apparatus 102, the item and the user which is indicative of the user wearing the item. In some such embodiments, a sensed human body temperature is indicative of the user wearing the item.

In embodiments, apparatus 102 is configured to operate multiple sensors in the plurality of sensors 104 to perform the determination. In some such embodiments, a voting mechanism between indications of the multiple sensors is employed in the determination. In some such embodiments, a weighting mechanism between indications of the multiple sensors is employed in the determination.

Figure 2:
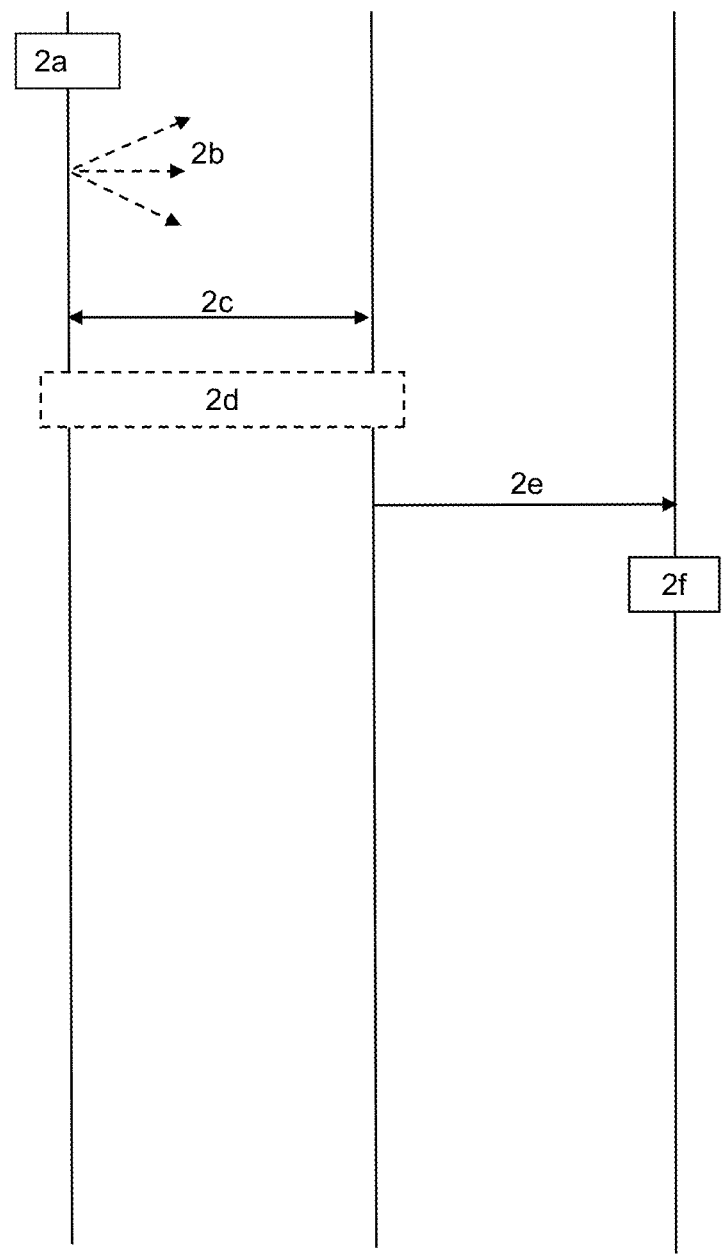
FIG. 2 shows a message flow diagram according to embodiments.

FIG. 2 shows a message flow diagram according to embodiments.

Item 2a depicts apparatus 102 positively determining that a user is wearing an item in which apparatus 102 is comprised, and so is operating in the active operating mode where one or more sensors in plurality 104 generate data associated with motion of the user at the first sampling rate. The one or more sensors may for example comprises one or more accelerometers or gyroscopes.

In embodiments, the active operating mode comprises apparatus 102 inserting at least a part of the data generated at the first sampling rate into advertising packets of a wireless communication protocol, and broadcasting the advertising packets comprising the data generated at the first sampling rate according to the wireless communication protocol as per item 2b. In embodiments, the active operating mode comprises apparatus 102 broadcasting the advertising packets comprising the data generated at the first sampling rate according to the wireless communication protocol at a first broadcasting frequency. The wireless communication protocol may for example comprise the BLE protocol.

In embodiments, the active operating mode comprises apparatus 102 analysing the data associated with motion of the user generated at the first sampling rate for an indication of an impact event associated with the user, and, in response to the analysing indicating occurrence of an impact event associated with the user, communicating, as per item 2c with remote device 110 to inform remote device 110 of the impact event associated with the user. In embodiments, remote device 110 may learn of the occurrence of the impact event via the broadcasting of item 2b.

In embodiments, the active operating mode comprises apparatus 102 establishing a data connection 2d with remote device 110, and transmitting data associated with the impact event associated with the user to the remote device via the data connection. In embodiments, the established data connection is a two-way (duplex) connection. Data transmitted via the data connection may for example be transmitted via a BLE protocol communication session. The data transmitted via the data connection may comprise high-resolution data relating to the impact event associated with the user.

In embodiments, remote device 110 notifies a server 120 of occurrence of the impact event associated with the user as per item 2e. The notification of item 2e may include some or all of the data associated with the impact event associated with the user which was transmitted to remote device 110 via the established data connection. In embodiments, in item 2f server analyses the data received in item 2e and may take remedial action such as contacting one or more emergency services to attend to or otherwise assist the user. In some embodiments, server 120 may comprise a server operated by the one or more emergency services such that a separate step of contacting the one or more emergency services can be omitted.

In alternative embodiments, remote device 110 analyses the data received in item 2e and may take remedial action such as contacting the one or more emergency services directly (instead of or in addition to server 120) in order for the user to receive assistance from the one or more emergency services.

Figure 3:
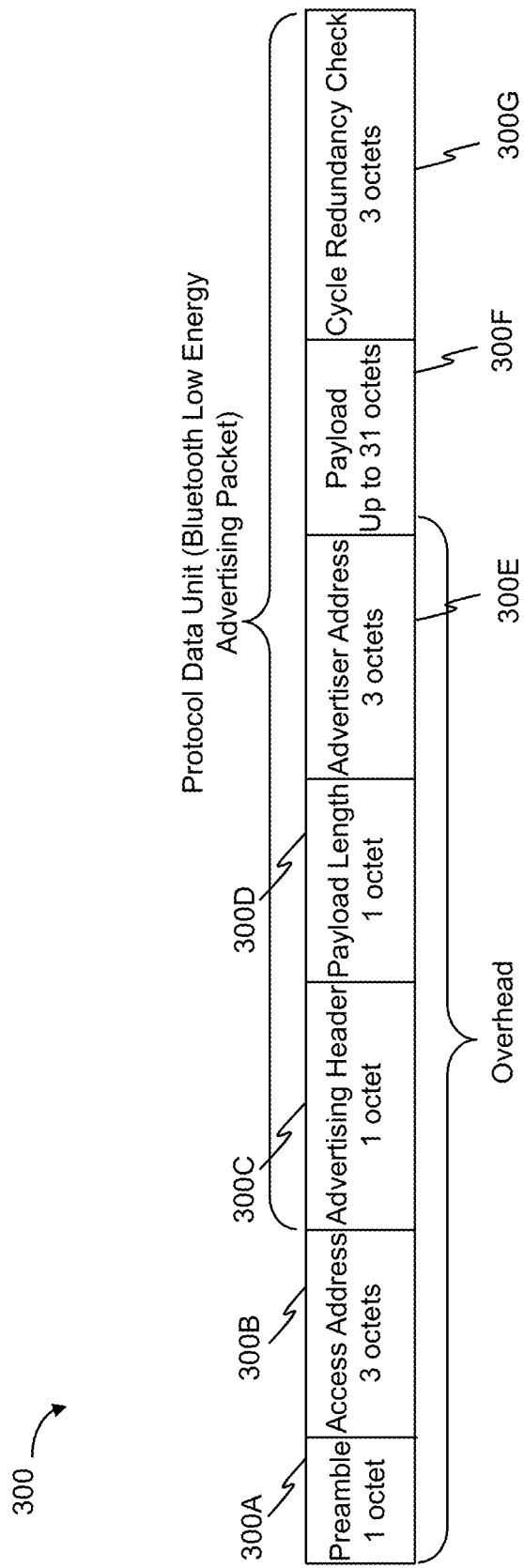
FIG. 3 shows a broadcast packet according to embodiments.

FIG. 3 shows a broadcast packet 300 according to embodiments. In these example embodiments, broadcast packet 300 comprises a BLE advertising packet. Broadcast packet 300 comprises a 1-octet (an 8-bit byte) preamble portion 300A, a 3-octet access address portion 300B, a 1-octet advertising header portion 300C, a 1-octet payload length portion 300D, a 3-octet advertiser address portion 300E, an up to 31-octet payload portion 300F and a 3-octet cyclic redundancy check portion 300G. The up to 31-octet payload portion 300F is intended (by Bluetooth core specification) to carry manufacturing specific data. In embodiments, apparatus 102 inserts generated data into manufacturing specific data portions of BLE advertising packets which apparatus 102 then broadcasts. In the embodiments of FIG. 3, generated data is inserted into payload portion 300F.

In embodiments, the active operating mode comprises apparatus 102, in response to the analyzing indicating occurrence of an impact event associated with the user, storing data associated with the impact event associated with the user on apparatus 102 (for example in one or more memories 102B).

In embodiments, the active operating mode comprises apparatus 102, in response to the analyzing indicating occurrence of an impact event associated with the user, comparing data associated with the impact event associated with the user with data stored on apparatus 102 associated with a prior impact event associated with the user. In response to the comparison indicating that the impact event associated with the user was more severe than the prior impact event associated with the user, apparatus 102 stores data associated with the impact event associated with the user on apparatus 102 in preference to data associated with the prior impact event associated with the user. In embodiments, data for multiple impacts associated with the user is stored on apparatus 102.

In embodiments, the indication of an impact event comprises an indication of gravitational acceleration above a predetermined gravitational acceleration threshold. The predetermined gravitational acceleration threshold may for example comprise one or more of 20 g, 100 g and 150 g (where 'g' comprises a gravitational acceleration of approximately 9.81 meters per second squared).

In embodiments, one or more magnetic elements are incorporated into a wearable item, for example into a helmet liner. Such embodiments can then use one or more magnetometers to detect the movement of the helmet around the helmet liner which is close to the head to better calculate the effect of the impact on the user.

In embodiments, the one or more sensors in the plurality 104 operated in the active operating mode comprise a magnetometer. In some such embodiments, the magnetometer is configured to monitor shear forces associated with the item.

In embodiments, the item comprises a helmet, apparatus 102 is incorporated into the helmet, and the magnetometer is comprised in the helmet and a magnetic element is incorporated in a liner of the helmet. The monitored shear forces may for example comprise shear forces generated between the helmet and the helmet liner. A shear sensor may be configured according to embodiments to measure shear in x and y directions and force in the z direction.

In embodiments, the one or more sensors in the plurality operated in the active operating mode comprise one or more accelerometers and the at least part of the data generated at the first sampling rate inserted into advertising packets of the wireless communication protocol comprises data generated by the one or more accelerometers.

In embodiments, apparatus 102 is configured to, in response to a negative determination (i.e. it is determined that the user is not wearing the item), first determine whether a first predetermined time period has elapsed, and, in response to a positive first determination, operate apparatus 102 in a deep sleep operating mode.

In embodiments, apparatus 102 is configured to, in response to a negative first determination second determine whether a second predetermined time period has elapsed. In embodiments, the second predetermined time period is shorter than the first predetermined time period. In response to a positive second determination, apparatus 102 is configured to operate apparatus 102 in a sleep operating mode.

In embodiments, the sleep operating mode comprises operating one or more sensors in plurality 104 to generate data associated with motion of the user at a second sampling rate lower than the first sampling rate. Generating data at the (lower) second sampling rate uses less power than generating data at the (higher) first sampling rate; the sleep operating mode is therefore a lower power consumption mode than the active operating mode.

In embodiments, the sleep operating mode comprises inserting at least a part of the data generated at the second sampling rate into advertising packets of a wireless communication protocol, and broadcasting the advertising packets comprising the data generated at the second sampling rate according to the wireless communication protocol. In embodiments, the sleep operating mode comprises broadcasting the advertising packets comprising the data generated at the second sampling rate according to the wireless communication protocol at a second broadcasting frequency.

In embodiments, the second broadcasting frequency is less than the first broadcasting frequency. Broadcasting data at the (lower) second broadcasting frequency uses less power than broadcasting data at the (higher) first broadcasting frequency; the sleep operating mode is therefore a lower power consumption mode than the active operating mode.

In embodiments, the deep sleep operating mode comprises operating one or more sensors in the plurality to generate data associated with motion of the user at a third sampling rate lower than the second sampling rate.

Generating data at the third sampling rate uses less power than generating data at the second sampling rate, which in turn uses less power than generating data at the first sampling rate; the deep sleep operating mode is therefore a lower power consumption mode than the sleep operating mode, which is in turn a lower power consumption mode than the active operating mode.

In embodiments, the deep sleep operating mode comprises inserting at least a part of the data generated at the third sampling rate into advertising packets of a wireless communication protocol, and broadcasting the advertising packets comprising the data generated at the third sampling rate according to the wireless communication protocol.

In embodiments, the deep sleep mode comprises broadcasting the advertising packets comprising the data generated at the third sampling rate according to the wireless communication protocol at a third broadcasting frequency.

In embodiments, the second broadcasting frequency is less than the first broadcasting frequency and the third broadcasting frequency is less than the second broadcasting frequency.

Broadcasting data at the third broadcasting frequency uses less power than broadcasting data at the second broadcasting frequency, which in turn uses less power than broadcasting data at the first broadcasting frequency; the deep sleep operating mode is therefore a lower power consumption mode than the sleep operating mode, which in turn is a lower power consumption mode than the active operating mode.

In embodiments, data from multiple sensors in plurality 104 on apparatus 102 is used to detect if a wearable item such as a helmet or other product (for example body armor or hip protection) is being worn or not and switches the apparatus 102 between "Active", "Sleep" and "Deep Sleep" modes. Using temperature, inductive and/or motion sensors, embodiments are able to ascertain if the product is being worn or used or if it is dormant and not being used and switch to the appropriate mode of operation using this data.

In embodiments, "Active" mode involves some or all sensors (for example accelerometers and gyroscopes) in plurality 104 being set to operate at a minimum of 1 kHz. Upon apparatus 102 triggering during an impact, apparatus 102 stores data from the sensors and compares it internally to any previously stored data. In some embodiments, if the new data shows a higher level of impact, the new data is stored and the old data discarded. Such embodiments allow the most significant impact data to be saved to the apparatus. In embodiments, full classification of the impact is not performed on-board the sensor(s) but upon detecting a high-g event (one that, for example, exceeds a pre-set threshold value, for example 150 g) apparatus 102 signals to remote device 110 (such as a mobile telephone) that it has data associated with an impact available. Remote device 110 then connects to apparatus 102, downloads the data from apparatus 201 and then either processes the data locally or transmits the data to server 120 for analysis. Once the impact has been confirmed by remote device 110 and/or server 120, an alert can be sent from remote device and/or server 120 to any number of receivers via text message, instant message email, phone call, etc. During this time, remote device 110 may also reset apparatus 102 so it is ready for the next impact or collision event.

In "Sleep" mode, some or all sensors in plurality 104 have sampling frequencies reduced to conserve power and the likelihood of detecting an impact is reduced. However, according to embodiments, in this mode, any wearable item in which apparatus 102 is incorporated will likely either not be being worn or not being actively used.

In "Deep Sleep" mode, the sampling frequency of some or all sensors in plurality 104 is reduced further and apparatus 102 stops being able to detect impacts/falls. The advertising period is also reduced to further save power. This mode is used when there is very little chance that the user is wearing an item in which apparatus 102 is incorporated.

In embodiments, in all three modes, data is encoded into the Manufacturing Specific Data area of BLE advert packets. The advert packets are detected by an in-range remote device 110 such as a smart phone scanning for a BLE device with a particular signature and data content. The data within the BLE advert can then be extracted, time-stamped and stored on board device 110. This data can then be transmitted to one or more servers 120. Such embodiments allow the user and relevant service operators to keep updated with the status of the apparatus.

In embodiments, apparatus 102 is configured to, in response to a negative determination, operate apparatus 102 in a mode other than the active operating mode. The mode other than the active operation mode comprises operating one or more sensors in the plurality to generate data associated with motion of the user at a sampling rate different from the first sampling rate. In embodiments, the mode other than the active operating mode comprises apparatus 102 inserting at least a part of the data generated at the sampling rate different from the first sampling rate into advertising packets of a wireless communication protocol, and broadcasting the advertising packets comprising the data generated at the sampling rate different from the first sampling rate according to the wireless communication protocol. In embodiments, the mode other than the active operating mode comprises apparatus 102 broadcasting the advertising packets comprising the data generated at the sampling rate different from the first sampling rate according to the wireless communication protocol at a broadcasting frequency different from the first broadcasting frequency. In embodiments, the sampling rate different from the first sampling rate is lower than the first sampling rate. In embodiments, the broadcasting frequency different from the first broadcasting frequency is lower than the first broadcasting frequency.

In embodiments, apparatus 102 is comprised within a helmet.

In embodiments, apparatus 102 is comprised within a wearable item. The wearable item may comprise one or more of a hip protector, a limb protector, a back protector, body armor, a glove, a jacket, a helmet, a sports garment, an activity monitoring garment, a sensor equipped garment, personal protective equipment, and a medical device.

In some embodiments, the first sampling rate is equal to (or approximately) 1 kHz. In other embodiments, the first sampling rate is greater than 1 kHz.

In some embodiments, the second sampling rate is equal to (or approximately) 10 Hz. In other embodiments, the second sampling rate is greater than 10 Hz, but less than 1 kHz.

In some embodiments, the third sampling rate is equal to (or approximately) 1 Hz. In other embodiments, the third sampling rate is less than 1 Hz.

In embodiments, the first broadcasting frequency is approximately once every 5 seconds. In other embodiments, the first broadcasting frequency is more than once every 5 seconds.

In embodiments, the second broadcasting frequency is approximately once every 5 seconds. In other embodiments, the second broadcasting frequency is more than once every 15 seconds, but less than once every 5 seconds.

In embodiments, the third broadcasting frequency is approximately once every 15 seconds. In other embodiments, the third broadcasting frequency is less than once every 15 seconds.

Embodiments comprise circuitry comprising a plurality of sensors, the circuitry being configured to: determine whether a user is wearing an item in which the circuitry is comprised; and in response to a positive determination, operate the circuitry in an active operating mode, wherein the active operating mode comprises operating one or more sensors in the plurality to generate data associated with motion of the user at a first sampling rate.

Embodiments comprise a method of operating apparatus comprising a plurality of sensors, the method comprising: determining whether a user is wearing an item in which the apparatus is comprised; and in response to a positive determination, operating the apparatus in an active operating mode, wherein the active operating mode comprises operating one or more sensors in the plurality to generate data associated with motion of the user at a first sampling rate.

Embodiments comprise a computer program comprising a set of instructions, which, when executed by a computerized device comprising a plurality of sensors, cause the computerized device to perform a method comprising: determining whether a user is wearing an item in which the device is comprised; and in response to a positive determination, operating the device in an active operating mode, wherein the active operating mode comprises operating one or more sensors in the plurality to generate data associated with motion of the user at a first sampling rate.

Embodiment comprise a device comprising a plurality of sensors, the device being configured to: operate the device in one of an active operating mode, a sleep operating mode and a deep sleep operating mode, wherein operating the device in the active operating mode comprises controlling one or more sensors in the plurality to generate data associated with motion of the user at a first sampling rate, wherein operating the device in the sleep operating mode comprises controlling one or more sensors in the plurality to generate data associated with motion of the user at a second sampling rate, the second sampling rate being less than the first sampling rate, and wherein operating the device in the deep sleep operating mode comprises controlling one or more sensors in the plurality to generate data associated with motion of the user at a third sampling rate, the third sampling rate being less than the second sampling rate.

In embodiments, operating the device in the active operating mode comprises inserting at least a part of the data generated at the first sampling rate into advertising packets of a wireless communication protocol, and broadcasting, at a first broadcasting frequency, the advertising packets comprising the data generated at the first sampling rate according to the wireless communication protocol.

In embodiments, operating the device in the sleep operating mode comprises inserting at least a part of the data generated at the second sampling rate into advertising packets of a wireless communication protocol, and broadcasting, at a second broadcasting frequency, the advertising packets comprising the data generated at the second sampling rate according to the wireless communication protocol.

In embodiments operating the device in the deep sleep operating mode comprises inserting at least a part of the data generated at the second sampling rate into advertising packets of a wireless communication protocol, and broadcasting, at a third broadcasting frequency, the advertising packets comprising the data generated at the second sampling rate according to the wireless communication protocol.

The second broadcasting frequency may for example be less than the first broadcasting frequency. The third broadcasting frequency may for example be less than the second broadcasting frequency.

Embodiments comprise a device comprising an impedance sensor, the device being incorporated into a wearable item, the device being configured to: operate the impedance sensor to measure an impedance associated with the item; and detect whether a user is currently wearing the item on the basis of the measured impedance.

Figure 4:
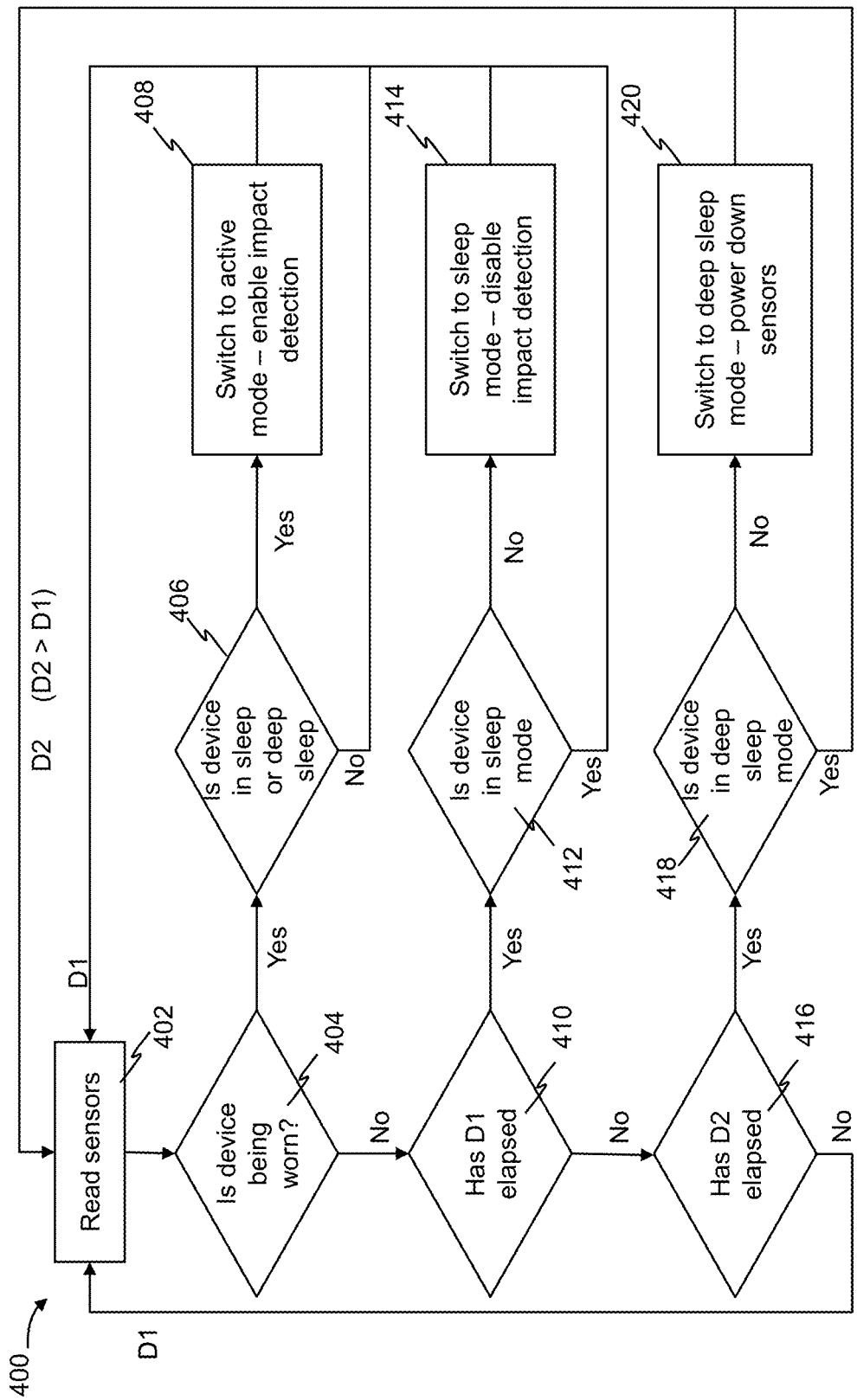
FIG. 4 shows a logic flow diagram according to embodiments.

FIG. 4 shows a logic flow diagram 400 according to embodiments. Flow diagram 400 depicts how apparatus 102 switches between an active operating mode, a sleep operating mode and a deep sleep operating mode according to embodiments.

Item 402 shows apparatus 102 reading one or more sensors in plurality 104. Flow then passes to item 404.

Item 404 shows apparatus 102 determining whether apparatus 102 is currently being worn by a user. If apparatus 102 determines that apparatus 102 is indeed being worn, then flow passes to item 406. If apparatus determines that apparatus 102 is not being worn, then flow passes to item 410.

In item 406, if apparatus 102 is operating in a sleep operating mode or a deep sleep operating mode, then flow passes to item 408. If apparatus 102 is not operating in a sleep operating mode or a deep sleep operating mode, then after a predetermined delay of D1, flow passes to item 402.

In item 408, apparatus 102 switches to an active operating mode in which impact detection is enabled and after a predetermined delay of D1, flow passes to item 402.

In item 410, apparatus 102 determines whether a predetermined delay of D1 has elapsed. If apparatus 102 determines that a predetermined delay of D1 has elapsed, then flow passes to item 412. If apparatus 102 determines that a predetermined delay of D1 has not elapsed, flow passes to item 416.

In item 412, if apparatus 102 is operating in a sleep operating mode, then after a predetermined delay of D1, flow passes to item 402. If apparatus 102 is not operating in a sleep operating mode, then flow passes to item 414.

In item 414, apparatus 102 switches to a sleep operating mode in which impact detection is disabled and after a predetermined delay of D1, flow passes to item 402.

In item 416, apparatus 102 determines whether a predetermined delay of D2 has elapsed. If apparatus 102 determines that a predetermined delay of D2 has elapsed, then flow passes to item 418. If apparatus 102 determines that a predetermined delay of D2 has not elapsed, then after a predetermined delay of D1, flow passes to item 402.

In item 418, if apparatus 102 is operating in a deep sleep operating mode, then after a predetermined delay of D2, flow passes to item 402. If apparatus 102 is not operating in a deep sleep operating mode, then flow passes to item 420.

In item 420, apparatus 102 switches to a deep sleep operating mode in which one or more (or all) sensors in plurality 104 are powered down and after a predetermined delay of D2, flow passes to item 402.

In embodiments, predetermined time delay D2 is a longer delay than predetermined time delay of D1. In embodiments, D2 may for example comprise 5 seconds. In embodiments, D1 may for example comprise 1 second. In embodiments, apparatus 102 comprises a timer function for monitoring/determining delay times; the timer function may for example be comprised within processor 102B or comprised within a separate timer chip in communication with processor 102B.

Figure 5:
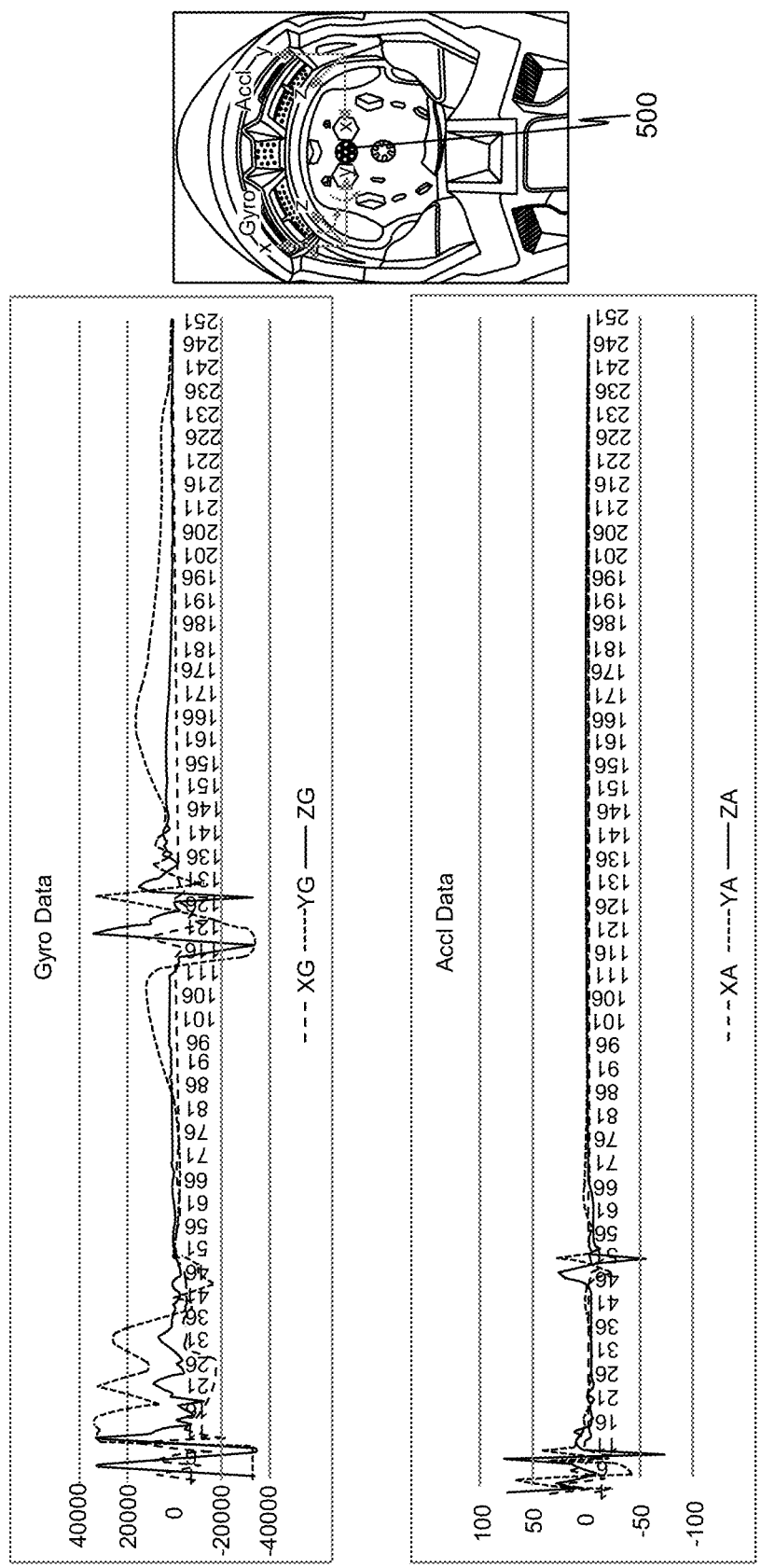
FIG. 5 shows signal plots for a front impact according to embodiments.
Figure 6:
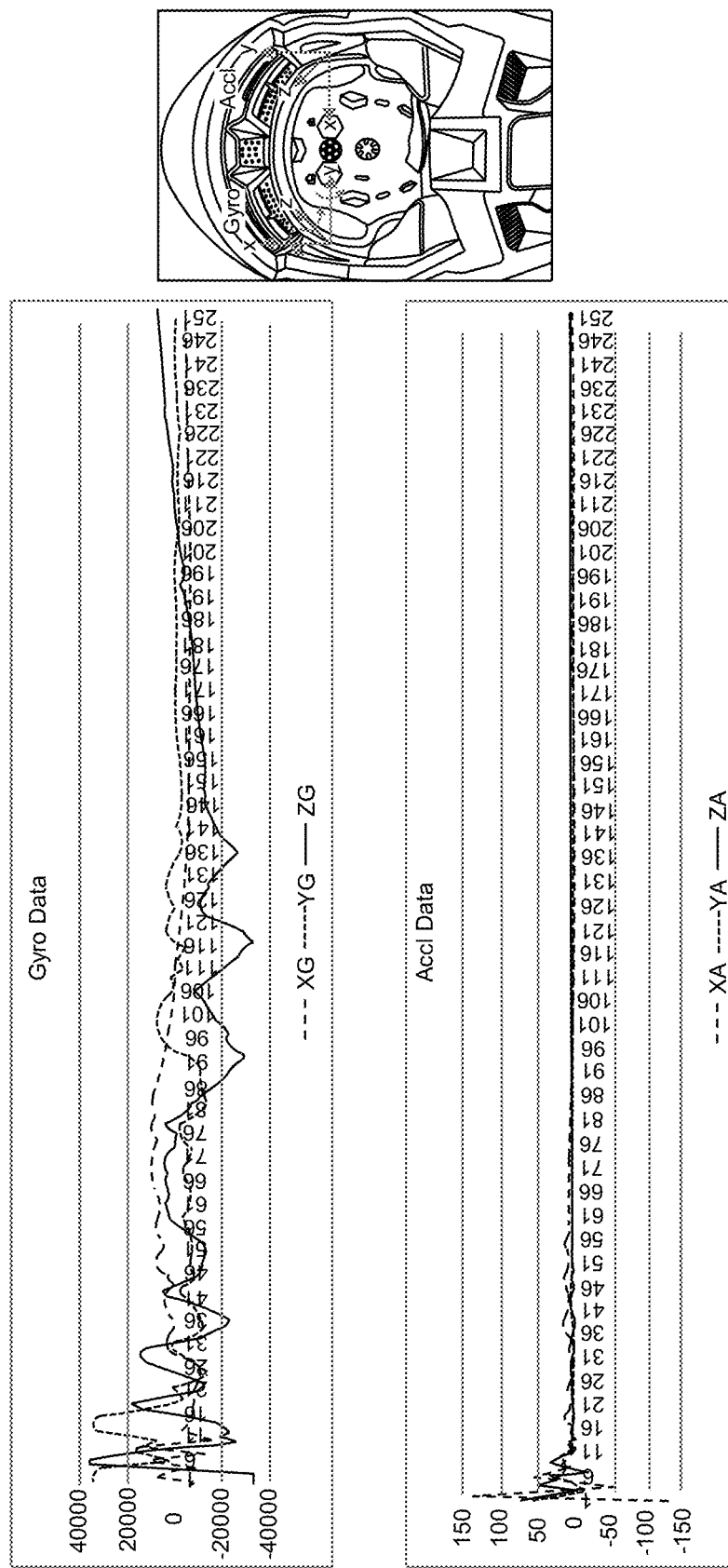
FIG. 6 shows signal plots for a side impact according to embodiments.

FIGS. 5 and 6 demonstrate how signals gathered according to embodiments during front and side impact tests respectively can be used to determine the direction and severity of impacts. In the embodiments depicted in FIGS. 5 and 6, apparatus 102 is integrated into a helmet. In these examples, apparatus 102 is comprised within a sealed enclosure 500 made of an energy absorbing material. In each case, plurality of sensors 104 comprises an accelerometer and a gyroscope and each of FIGS. 5 and 6 depict the orientation of the accelerometer ("Accl") and gyroscope ("Gyro"). Gold standard equipment was used during each test.

FIG. 5 shows gathered signal plots for a front impact according to embodiments. The signals were gathered using apparatus 102 incorporated into a helmet which was then subjected to an impact from a direction in front of the helmet. The example embodiments of FIG. 5 show high acceleration in the 'y' and 'z' axes for the accelerometer and a high rotation around the 'y' axis for the gyroscope.

FIG. 6 shows gathered signal plots for a side impact according to embodiments. The signals were gathered using apparatus 102 incorporated into a helmet (at the same orientation as for the front impact of FIG. 5) which was then subjected to an impact from a direction to the side of the helmet. The example embodiments of FIG. 6 show a high acceleration in the 'x' axis for the accelerometer and high rotation around the 'y' and 'z' axes for the gyroscope.

Further, in both cases, the amplitude and duration of the periods of high acceleration and rotation can be used to determine the severity of the impact.

The results depicted in FIGS. 5 and 6 are consistent with what is expected and other test data measured using gold standard equipment.

For head impact detection, the device could be held close to the skin in a tight-fitting cap or in the soft comfort liner of a helmet. In a helmet, the device could be incorporated into the energy absorbing liner below the crown area at the rear of the helmet. Typically, the energy absorbing liner is thick here and the presence of the device has been shown not to limit the energy absorbing properties of the helmet in certain test standards.

A good location for the sensor is towards the back of the crown. This is due to the combination of good overall readings and maximizing the distance from the most likely impact zone (shown to be the front of the helmet). The thickness of energy absorbing materials or expanded polystyrene (EPS) are also usually higher here in most helmets. Little difference was seen whether with and without the sensor for normal Department of Transportation (DOT) and Economic Commission for Europe (ECE) testing, when the device has been sealed in a soft energy absorbing material.

In embodiments, the device is placed close to the skin, so that the "shear sensor" can give a reading of force (normal direction) and shear in X and Y directions.

Element 500 in FIG. 5 shows the location of the device and proximity to the head according to embodiments. In these embodiments, the device is located in the middle of the helmet equally spaced between the two origins of the graphs.

Figure 7A:
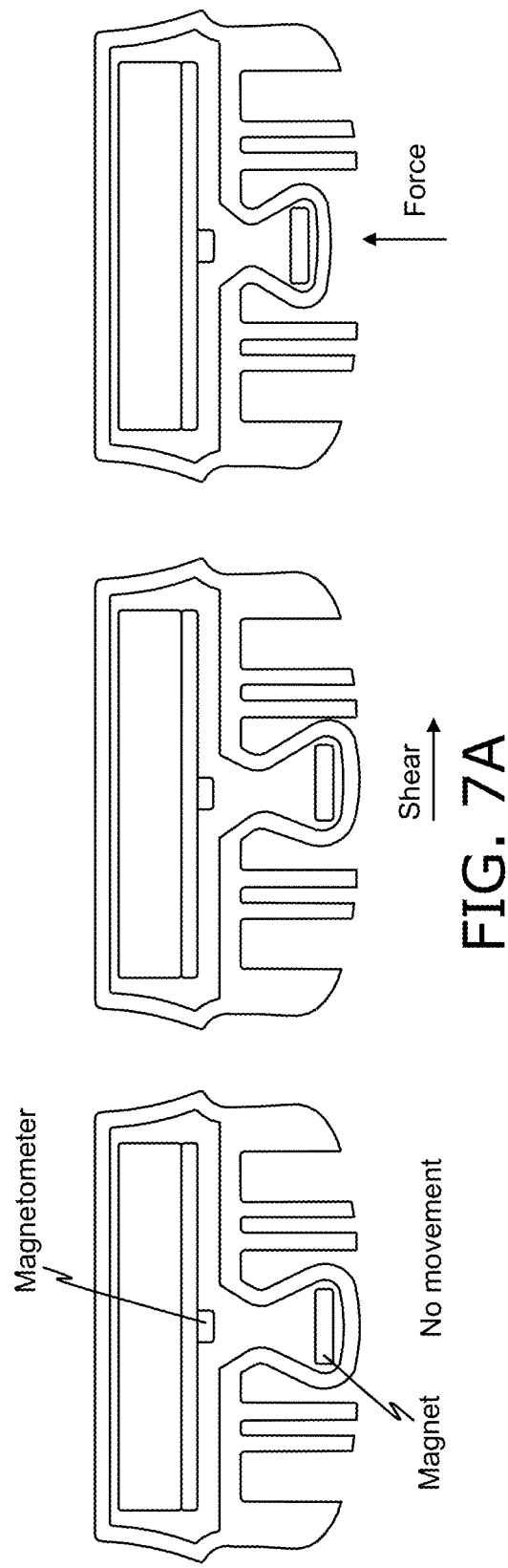
FIG. 7A shows a magnetometer according to embodiments.

FIG. 7A shows a magnetometer according to embodiments. In embodiments, a shear sensor and force sensor are employed comprising a magnet supported in soft encapsulation materials and in proximity to a magnetometer. In one embodiment, the device will have at least one magnetometer and above/below the magnetometer in its simplest form is a magnet. The magnet may comprise a small neodymium magnet molded into the soft protective packaging of the sensor. The example embodiments of FIG. 7A employ a re-entrant geometry.

A magnetometer and magnet together can act as a shear sensor according to embodiments. Having a shear sensor pointing towards the skull at this point can give an insight into the shear forces between the head and the helmet. This will give force measurements in the Z (through thickness) axis, and motions in X (sagittal) and Y (coronal) axes.

Figure 7B:
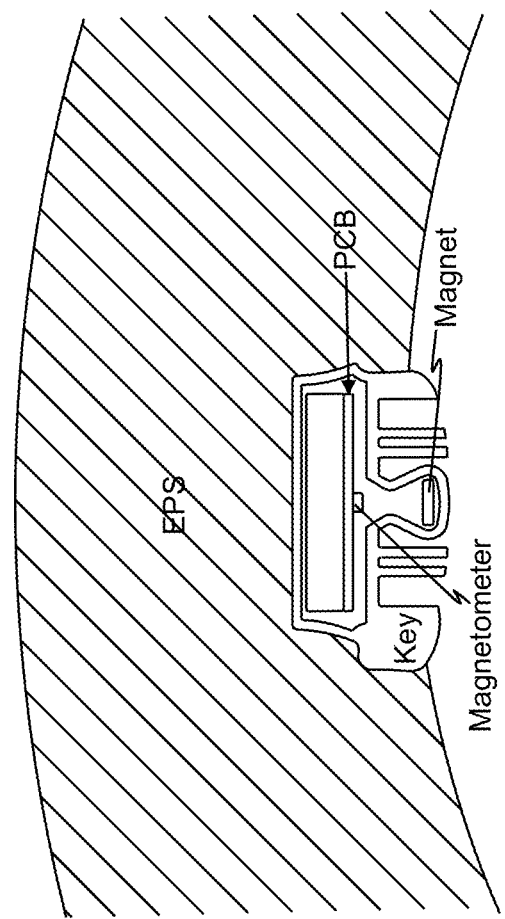
FIG. 7B shows a magnetometer located in a helmet liner according to embodiments.

FIG. 7B shows a magnetometer located in a helmet liner according to embodiments. Softer, thinner magnets can also be attached to a comfort liner within the helmet. Helmet liners typically move within the helmet during high rotational impacts, so the shear can be measured between the sensor in the helmet, and the surface of the liner which approximates the head/skull movement.

Figure 8:
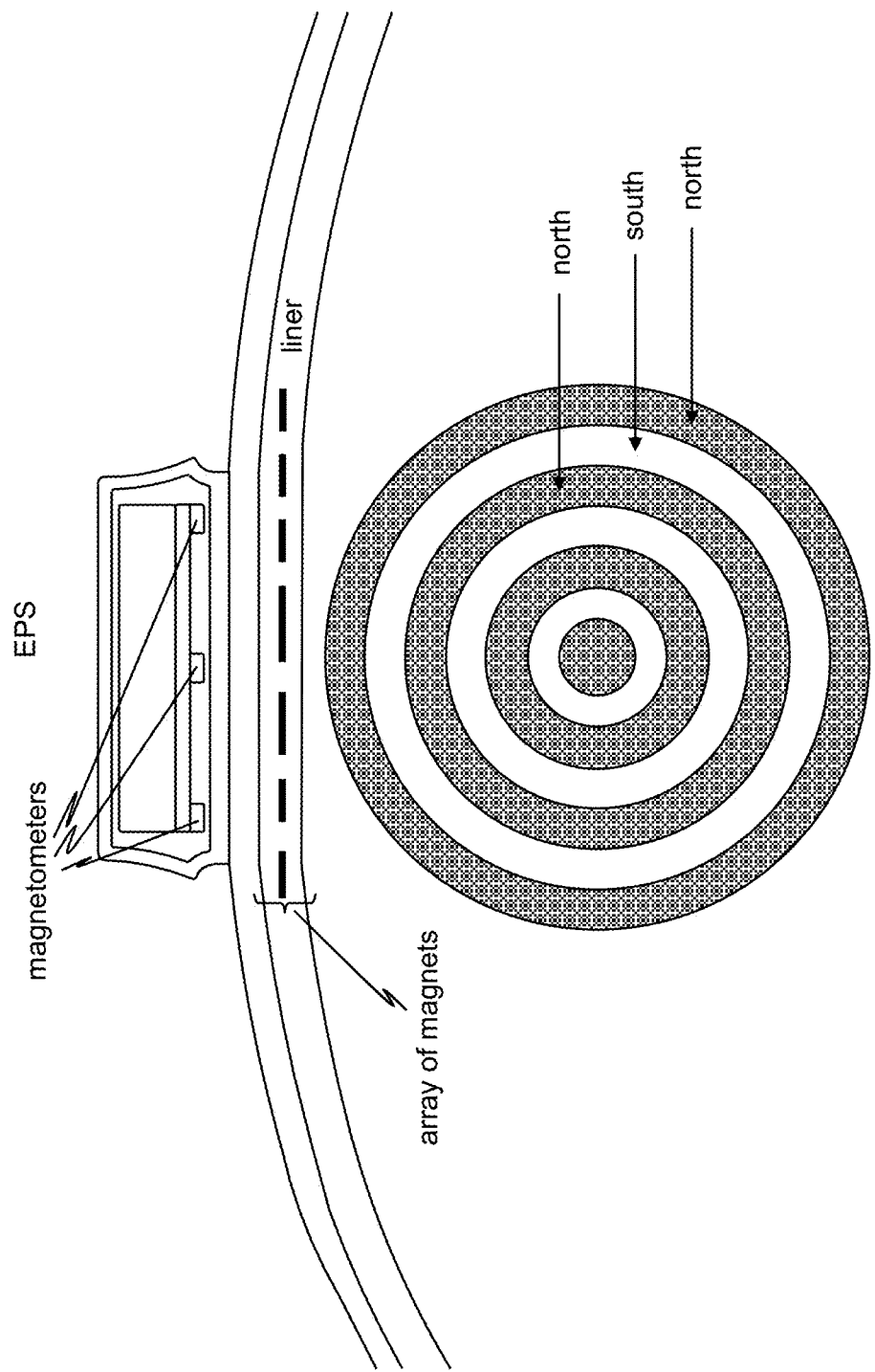
FIG. 8 shows multiple magnetometers according to embodiments.

FIG. 8 shows multiple magnetometers according to embodiments. In the example embodiments of FIG. 8, three magnetometers are employed in a helmet.

Embodiments may employ multiple magnetometers to give a Vernier scale and vector direction. Such embodiments enable measuring of shear within a helmet in conjunction with multiple soft magnets in the liner. The magnets can be put in an array of North-/South-/-North to give extended measurements. In embodiments, an advanced sensor uses an array of magnets, for example in the shape of a target (concentric circles) with rings of alternating magnetic poles in the helmet liner as depicted in FIG. 8.

In alternative embodiments, an optical scale is employed with a grating in the liner, and relative optoelectronics on a circuit board (light emitting diode (LED) and sensor) which can be coupled with multiple sensors if needed.

The magnetometer of embodiments can be zeroed from time to time. The system can be calibrated in a helmet during impact testing in linear and oblique conditions, and has shown good correlation with magnitude and direction of impact.

In medical fall detection or other such applications, the device could be incorporated into a close-fitting garment or attached near to the top of a user's greater trochanter (bone). This would allow the device to collect data on movement of the femur which sits close to the skin. Alternatively, the device could be held close to the skin on the lower back, in an undergarment for example. The device could similarly be incorporated into a shoe insole to collect data from the movement of the user's foot. These locations could be used to measure key variables in user's gait, to measure increasing changes in gait over time or as a predictor for fracture of the neck or the femur or other injury from a fall. By analyzing changes in gait, it is possible to predict the likelihood of a future fall event.

Tests according to embodiments have shown that data collected from devices held closer to the skin (compared to devices held further away) is of a better quality and more valuable for analysis purposes.

Figures 9A, 9B, 9C:
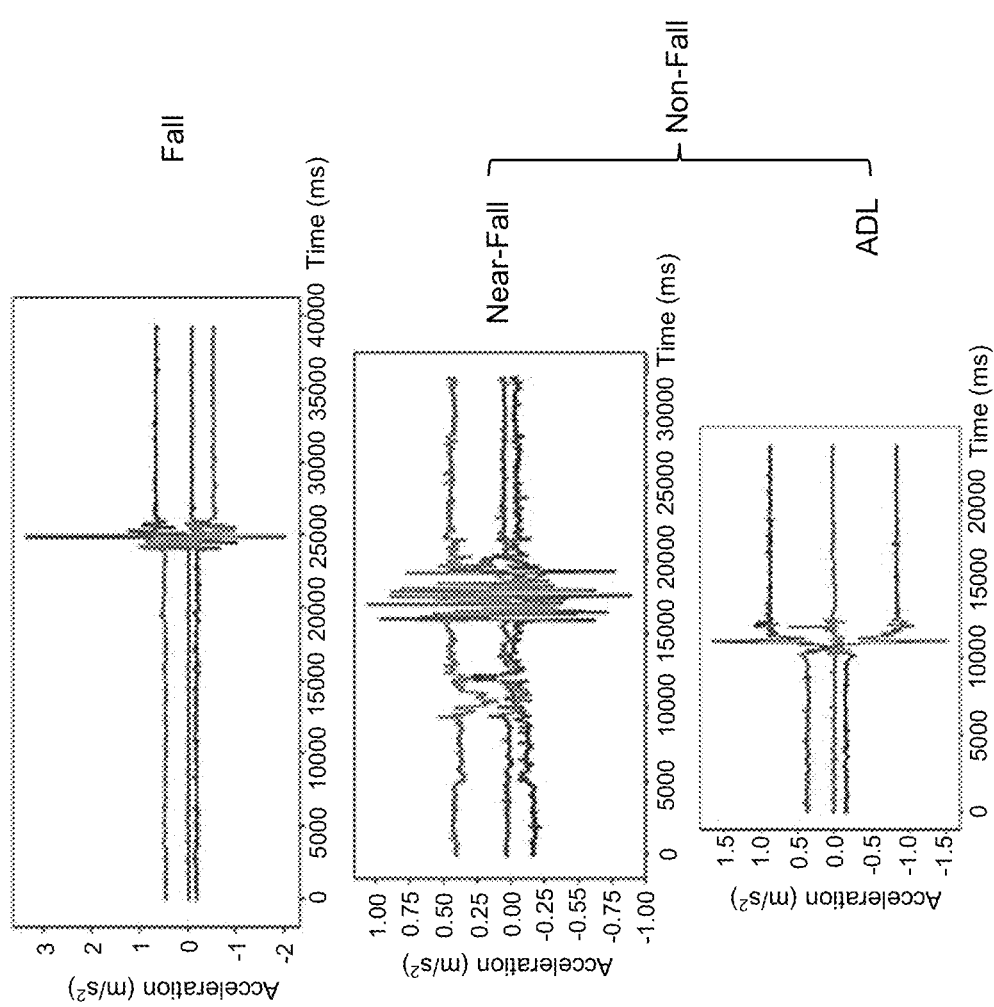
FIGS. 9A to 9C show test data according to embodiments.

FIGS. 9A to 9C show test data according to embodiments.

FIG. 9A shows test data for devices positioned at three different locations on the body for detecting falls and their associated impacts. The devices are molded into a protective pad which is placed near to the greater trochanter on the femur on both the left and right sides of the body as well as the rear of the waistband of the holster (near the base of the spine). The devices were over molded and held body close and were named left thigh (LT), right thigh (RT) and lower back (LB) for each position respectively.

Falls, near falls and Activities of Daily Living (ADL) were simulated with typical traces recorded from each of the devices shown in FIG. 9. A fall can be seen through a reduction in vector G less than a threshold, followed by an impact, then a change in orientation. The signature characteristic of a fall is different from a near fall or ADL.

In these embodiments, three sensors were used in different locations (LT, RT and LB) for 15 participants and 967 activities.

FIG. 9B shows average accuracy and it can be seen that there was a small improvement in system performance when dropping sampling frequency to 25 Hz. This means that a lower frequency could further enhance battery life.

FIG. 9C shows average accuracy and it can be seen that combining three sensors gives the best fall prediction, but using two sensors does not significantly lower the system performance. In terms of sensor placement, the LT and RT locations performed the best.

Whilst the present disclosure has been described and illustrated with reference to particular embodiments, it will be appreciated by those of ordinary skill in the art that the present disclosure lends itself to many different variations not specifically illustrated herein. By way of example only, certain possible variations will now be described.

Some embodiments have been described above in relation to an apparatus and others in relation to a device or a combination of the two; the terms "apparatus" and "device" can be used interchangeably and any embodiments described in relation to one are equally applicable in relation to the other.

Some embodiments described above involve triggering a mode change of the apparatus/device upon occurrence of a high g event. In other embodiments, triggering of a mode change of the apparatus/device occurs for "zero G events" (low impact events where g values are relatively low, for example approaching or equal to zero in one or more directions/sensors or approaching or equal to zero when averaged across multiple directions/sensors). Such zero G events may for example involve low impact incidents on a road bicycle or suchlike, where, even at low impact levels, it can be useful to collect sensor data.

In embodiments described above, apparatus 102 comprises a plurality of sensors 104. In alternative embodiments, apparatus 102 comprises a single sensor which is capable of sensing multiple parameters. In embodiments, sensors in plurality of sensors 104 are located spatially apart in order to allow spatial sensing of parameters.

In embodiments described above, apparatus 102 broadcasts data using a wireless communications protocol such as Bluetooth, for example via a Bluetooth communications transceiver of apparatus 102. In alternative embodiments, apparatus 102 comprises a mobile telephone (or "cellular") network transceiver, and apparatus 102 broadcasts data via a wireless communication protocol which comprises a mobile telephone network communication protocol.

Embodiments have been described above in relation to impact detection. Embodiments can also be employed more generally in user activity monitoring, for example in monitoring sleep cycles of (elderly) people, developing cooling systems for helmets, etc.

In embodiments described above, apparatus 102 operates as a single unit integrated into, for example, a helmet. In alternative embodiments, multiple units are employed, for example incorporated in an array arrangement, to allow the quality of gathered data to be increased.

FIG. 4 depicts an example state logic flow for apparatus 102. In alternative embodiments, different logic for switching between any states of apparatus 102 to that depicted in FIG. 4 may be employed.

Where in the foregoing description, integers or elements are mentioned which have known, obvious or foreseeable alternatives, then such alternatives are herein incorporated as if individually set forth. Reference should be made to the claims for determining the true scope of the present disclosure, which should be construed so as to encompass any such alternatives. It will also be appreciated by the reader that integers or features of embodiments that are described as preferable, advantageous, convenient, or the like are optional and do not limit the scope of the independent claims. Moreover, it is to be understood that such optional integers or features, whilst of possible benefit in some embodiments, may not be desirable, and may therefore be absent, in other embodiments.

What is claimed is:

1. An apparatus comprising a plurality of sensors and configured to:
   determine whether a user is wearing an item in which the apparatus is comprised; and
   in response to a positive determination:
      operate the apparatus in an active operating mode, wherein the active operating mode comprises operating one or more sensors in the plurality to generate data associated with motion of the user at a first sampling rate;
   in response to a negative determination:
      first determine whether a first predetermined time period has elapsed;
      in response to a positive first determination, operate the apparatus in a deep sleep operating mode;
      in response to a negative first determination, second determine whether a second predetermined time period has elapsed, the second predetermined time period being shorter than the first predetermined time period; and
      in response to a positive second determination, operate the apparatus in a sleep operating mode.

2. The apparatus according to claim 1, wherein:
   the deep sleep operating mode consumes less power than the sleep operating mode, and
   the sleep operating mode consumes less power than the active operating mode.

3. The apparatus according to claim 1, wherein in the active operating mode, the apparatus is further configured to:
   insert at least a part of the data generated at the first sampling rate into advertising packets of a wireless communication protocol;
   broadcast the advertising packets comprising the data generated at the first sampling rate according to the wireless communication protocol; and
   broadcast the advertising packets comprising the data generated at the first sampling rate according to the wireless communication protocol at a first broadcasting frequency.

4. The apparatus according to claim 1, wherein in the sleep operating mode, the apparatus is further configured to:
   operate one or more sensors in the plurality to generate data associated with motion of the user at a second sampling rate lower than the first sampling rate,
   insert at least a part of the data generated at the second sampling rate into advertising packets of a wireless communication protocol; and
   broadcast, at a second broadcasting frequency, the advertising packets comprising the data generated at the second sampling rate according to the wireless communication protocol.

5. The apparatus according to claim 4, wherein in the deep sleep operating mode, the apparatus is further configured to:
   operate one or more sensors in the plurality to generate data associated with motion of the user at a third sampling rate;
   insert at least a part of the data generated at the third sampling rate into advertising packets of a wireless communication protocol; and
   broadcast, at a third broadcasting frequency, the advertising packets comprising the data generated at the third sampling rate according to the wireless communication protocol.

6. The apparatus according to claim 3, wherein:
   in the sleep operating mode, the apparatus is further configured to:
      operate one or more sensors in the plurality to generate data associated with motion of the user at a second sampling rate lower than the first sampling rate,
      insert at least a part of the data generated at the second sampling rate into advertising packets of a wireless communication protocol; and
      broadcast, at a second broadcasting frequency, the advertising packets comprising the data generated at the second sampling rate according to the wireless communication protocol, and
   the second broadcasting frequency is less than the first broadcasting frequency.

7. The apparatus according to claim 4, wherein:
   in the deep sleep operating mode, the apparatus is further configured to:
      operate one or more sensors in the plurality to generate data associated with motion of the user at a third sampling rate lower than the second sampling rate;
      insert at least a part of the data generated at the third sampling rate into advertising packets of a wireless communication protocol; and
      broadcast, at a third broadcasting frequency, the advertising packets comprising the data generated at the third sampling rate according to the wireless communication protocol, and
   the third broadcasting frequency is less than the second broadcasting frequency.

8. The apparatus according to claim 1, wherein:
   the apparatus is encapsulated within a sealed enclosure,
   the sealed enclosure comprises a strain rate sensitive material and/or an energy absorbing material, and/or the apparatus comprises a non-rechargeable battery, wherein the non-rechargeable battery is encapsulated within the sealed enclosure.

9. The apparatus according to claim 1, wherein the apparatus is configured to operate at least one sensor in the plurality to perform the determination.

10. The apparatus according to claim 9, wherein:
the at least one sensor operated to perform the determination comprises an impedance sensor operable to determine whether the user is wearing the item by sensing an impedance indicative of the user wearing the item,
a sensed impedance above a predetermined threshold is indicative of the user wearing the item, and
a sensed impedance below a predetermined threshold is indicative of the user not wearing the item.

11. The apparatus according to claim 9, wherein:
the at least one sensor operated to perform the determination comprises at least one accelerometer operable to determine whether the user is wearing the item by sensing movement and orientation of the apparatus indicative of the user wearing the item,
movement of the apparatus and the apparatus being orientated a predefined way up are indicative of the user wearing the item,
movement of the apparatus and the apparatus being orientated differently from the predefined way up are indicative of the user not wearing the item, and/or
no sensed movement of the apparatus is indicative of the user not wearing the item.

12. The apparatus according to claim 9, wherein:
the at least one sensor operated to perform the determination comprises at least one temperature sensor operable to determine whether the user is wearing the item by sensing a temperature of one or more of the apparatus, the item, and the user which is indicative of the user wearing the item, and
a sensed human body temperature is indicative of the user wearing the item.

13. The apparatus according to claim 1, wherein:
the apparatus is configured to operate multiple sensors in the plurality to perform the determination, and
one or more of a voting mechanism or a weighting mechanism between indications of the multiple sensors is employed in the determination.

14. The apparatus according to claim 1, wherein in the active operating mode, the apparatus is further configured to:
analyze the data associated with motion of the user generated at the first sampling rate for an indication of an impact event associated with the user;
in response to an indication of an impact event associated with the user:
communicate with a remote device to inform the remote device of the impact event associated with the user; and
store data associated with the impact event associated with the user on the apparatus;
establish a data connection with the remote device; and
transmit data associated with the impact event associated with the user to the remote device via the data connection,
wherein the remote device comprises one or more of a mobile telephone or a wireless access point.

15. The apparatus according to claim 14, wherein in the active operating mode, the apparatus is further configured to:
in response to an indication of an impact event associated with the user, compare data associated with the impact event associated with the user with data stored on the apparatus associated with a prior impact event associated with the user; and
in response to the comparison indicating that the impact event associated with the user was more severe than the prior impact event associated with the user, store data associated with the impact event associated with the user on the apparatus in preference to data associated with the prior impact event associated with the user.

16. The apparatus according to claim 1, wherein:
the one or more sensors in the plurality operated in the active operating mode comprise a magnetometer, and
the magnetometer is configured to monitor shear forces associated with the item.

17. The apparatus according to claim 16, wherein:
the item comprises a helmet,
the apparatus is incorporated into the helmet,
the magnetometer is comprised in the helmet,
a magnetic element is incorporated in a liner of the helmet, and
the monitored shear forces comprise shear forces generated between the helmet and the liner of the helmet.

18. The apparatus according to claim 3, wherein:
the one or more sensors in the plurality operated in the active operating mode comprise one or more accelerometers, and
the at least part of the data generated at the first sampling rate inserted into advertising packets of the wireless communication protocol comprises data generated by the one or more accelerometers.

19. A method of operating an apparatus comprising a plurality of sensors, the method comprising:
determining whether a user is wearing an item in which the apparatus is comprised; and
in response to a positive determination:
operating the apparatus in an active operating mode, wherein the active operating mode comprises operating one or more sensors in the plurality to generate data associated with motion of the user at a first sampling rate;
in response to a negative determination:
first determining whether a first predetermined time period has elapsed;
in response to a positive first determination, operating the apparatus in a deep sleep operating mode;
in response to a negative first determination, second determining whether a second predetermined time period has elapsed, the second predetermined time period being shorter than the first predetermined time period; and
in response to a positive second determination, operating the apparatus in a sleep operating mode.

20. A non-transitory computer readable medium storing code for impact detection, the code comprising instructions executable by a processor to:
determine whether a user is wearing an item in which the computerized device is comprised; and
in response to a positive determination:
operate the computerized device in an active operating mode,
wherein the active operating mode comprises operating one or more sensors in a plurality of sensors to generate data associated with motion of the user at a first sampling rate;
in response to a negative determination:

first determine whether a first predetermined time period has elapsed;

in response to a positive first determination, operate the computerized device in a deep sleep operating mode;

in response to a negative first determination, second determine whether a second predetermined time period has elapsed, the second predetermined time period being shorter than the first predetermined time period; and in response to a positive second determination, operate the computerized device in a sleep operating mode.

21. A device comprising a plurality of sensors, the device being configured to:

operate the device in one of an active operating mode, a sleep operating mode, and a deep sleep operating mode, wherein:

the device in the active operating mode is configured to control one or more sensors in the plurality to generate data associated with motion of a user of the device at a first sampling rate, the device in the sleep operating mode is configured to control one or more sensors in the plurality to generate data associated with motion of the user at a second sampling rate, the second sampling rate being less than the first sampling rate, and the device in the deep sleep operating mode is configured to control one or more sensors in the plurality to generate data associated with motion of the user at a third sampling rate, the third sampling rate being less than the second sampling rate.

* * * * *